US00PP24102P2

(12) United States Plant Patent
Hennen

(10) Patent No.: US PP24,102 P2
(45) Date of Patent: Dec. 17, 2013

(54) *SCHEFFLERA* PLANT NAMED 'AMATE SOLEIL'

(50) Latin Name: *Schefflera actinophylla*
Varietal Denomination: Amate Soleil

(75) Inventor: Gary Hennen, Alford, FL (US)

(73) Assignee: Oglesby Plants International, Altha, FL (US)

( * ) Notice: Subject to any disclaimer, the term of this patent is extended or adjusted under 35 U.S.C. 154(b) by 84 days.

(21) Appl. No.: 13/374,199

(22) Filed: Dec. 14, 2011

(51) Int. Cl.
*A01H 5/00* (2006.01)

(52) U.S. Cl.
USPC ..... Plt./377

(58) Field of Classification Search
USPC ..... Plt./377
See application file for complete search history.

(56) References Cited

PUBLICATIONS

UPOV-Pluto Plant Variety Database, Jun. 2012, citation for 'Soleil'.*

* cited by examiner

*Primary Examiner* — Susan McCormick Ewoldt
(74) *Attorney, Agent, or Firm* — Cassandra Bright

(57) ABSTRACT

A new and distinct *Schefflera* cultivar named 'Amate Soleil' is disclosed, characterized by bright yellow-green foliage coloration of both young and mature foliage. 'Amate Soleil' has characteristically short internodes and short leaf petioles, and an overall small leaf blade. Plant habit is uniquely suited for 15 to 30 cm pots. The new variety is a *Schefflera*, normally produced as an indoor ornamental container plant.

3 Drawing Sheets

Figure 1:
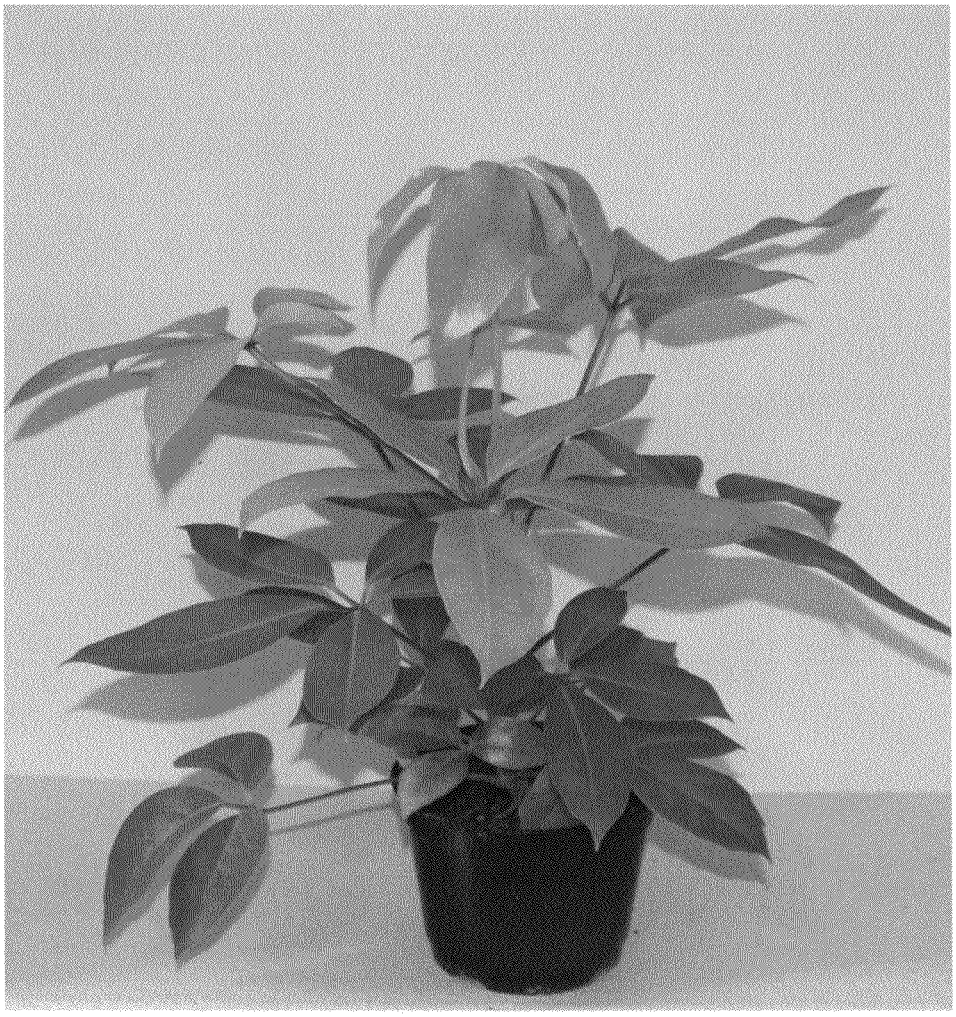

Latin name of the genus and species: *Schefflera actinophylla.*

Variety denomination: 'Amate Soleil'.

BACKGROUND OF THE INVENTION

The new *Schefflera* cultivar is a product of chance discovery by the inventor, Gary Hennen, a citizen of the United States. The discovery resulting in this new variety was made September 2006, by Gary Hennen at a commercial nursery in Altha, Fla.

The parent is the unpatented variety *Schefflera actinophylla* 'Amate'. The new variety was discovered as a naturally occurring whole plant mutation among a population of motherstock plants used for commercial production of the parent variety.

First asexual reproduction of the new cultivar 'Amate Soleil' was performed by tissue culture at a commercial laboratory in Altha, Fla. in March of 2008. Subsequently vegetative cuttings have also been made. Multiple generations have been produced, and have shown that the unique features of this cultivar are stable and reproduced true to type in successive generations.

SUMMARY OF THE INVENTION

The cultivar 'Amate Soleil' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Amate Soleil'. These characteristics in combination distinguish 'Amate Soleil' as a new and distinct *Schefflera* cultivar:

1. Bright Yellow-Green color of young and mature leaves.
2. Short internodes.
3. Short leaf petioles.
4. Smaller leaf blade relative to other *Schefflera actinophylla*
5. Plant habit suitable for 15 to 30 cm pots.

PARENT COMPARISON

Plants of the new cultivar 'Amate Soleil' are comparable to the parent *Schefflera actinophylla* 'Amate', unpatented. The two *Schefflera* varieties are similar in most horticultural characteristics however, the new variety 'Amate Soleil' differs in having bright yellow-green foliage, in both immature and mature stages, whereas foliage of 'Amate' is green. Additionally plants of 'Amate Soleil' are significantly shorter and somewhat narrower than plants of 'Amate', developing a fuller, less open plant than 'Amate'. 'Amate Soleil' has a smaller leaf in both width and length than 'Amate', and shorter petioles. 'Amate Soleil' has shorter internodes than the parent variety as well.

COMMERCIAL COMPARISON

Plants of the new cultivar 'Amate Soleil' are comparable to the variety *Schefflera actinophylla* 'Alpine Junior', unpatented. The two *Schefflera* varieties are similar in most horticultural characteristics however, the new variety 'Amate Soleil' differs having bright yellow-green foliage, in both immature and mature stages, whereas foliage of 'Alpine Junior' is always green. Additionally plants of 'Amate Soleil' are significantly shorter and somewhat narrower than plants of 'Alpine Junior'. 'Amate Soleil' has a smaller leaf in both width and length than 'Alpine Junior', and longer petioles. Plants of 'Amate Soleil' have shorter leaflet petioles than 'Alpine Junior'.

Plants of the new cultivar 'Amate Soleil' can be compared to the commercial variety 'Paradise', U.S. Plant Pat. No. 11,266. Plants are similar in many horticultural characteristics, however, 'Amate Soleil' has foliage which is bright yellow-green, compared to the dark green of 'Paradise'. Additionally, plants of 'Amate Soleil' are more open and spreading than the upright denser plants of 'Paradise'. Plants of 'Amate Soleil' have slower, more controlled growth and smaller foliage than plants of 'Paradise'.

Plants of the new cultivar 'Amate Soleil' are comparable to the commercial variety *Schefflera arboricola* 'Big Leaf', unpatented. The two *Schefflera* varieties are similar in most horticultural characteristics however, plants of the new variety 'Amate Soleil' differ in having bright yellow-green foliage, in both immature and mature stages, whereas foliage of 'Big Leaf' is green or dark green. Additionally plants of 'Amate Soleil' are somewhat shorter and slightly wider than plants of 'Big Leaf'. 'Amate Soleil' has a larger leaf in both width and length than 'Big Leaf', and longer, thicker petioles. Plants of 'Amate Soleil' have shorter leaflet petioles than 'Big Leaf'. Additionally, 'Amate Soleil' has significantly shorter internodes than 'Big Leaf'.

BRIEF DESCRIPTION OF THE PHOTOGRAPHS

FIG. 1: Illustrates in full color a plant of 'Amate Soleil' in a 6 inch pot, approximately 35 weeks old.

Figure 2:
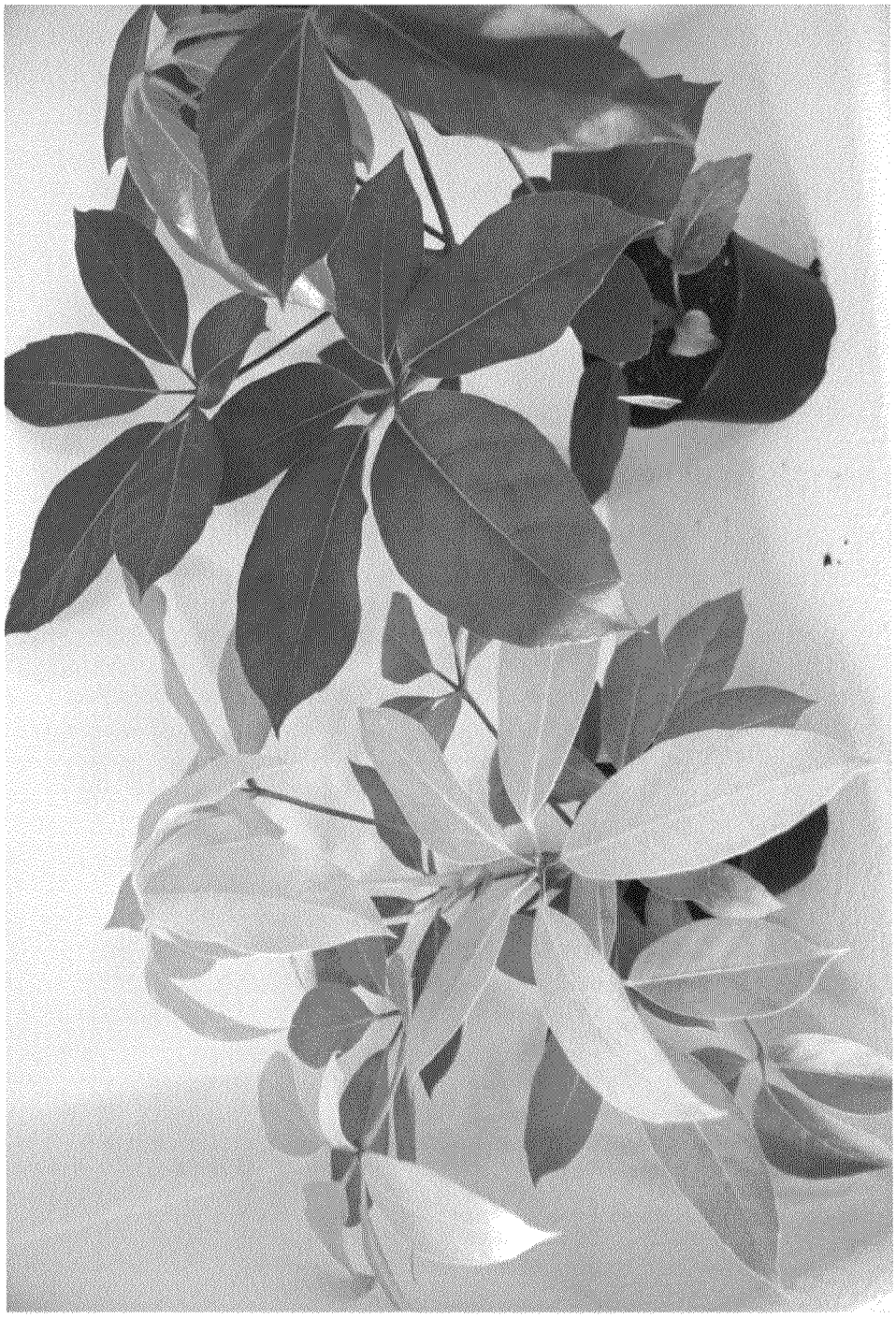

FIG. 2: Shows a comparison of plants of 'Amate Soleil' with the standard parent variety 'Amate', both in 6 inch pots. Plants are the same age, approximately 35 weeks.

Figure 3:
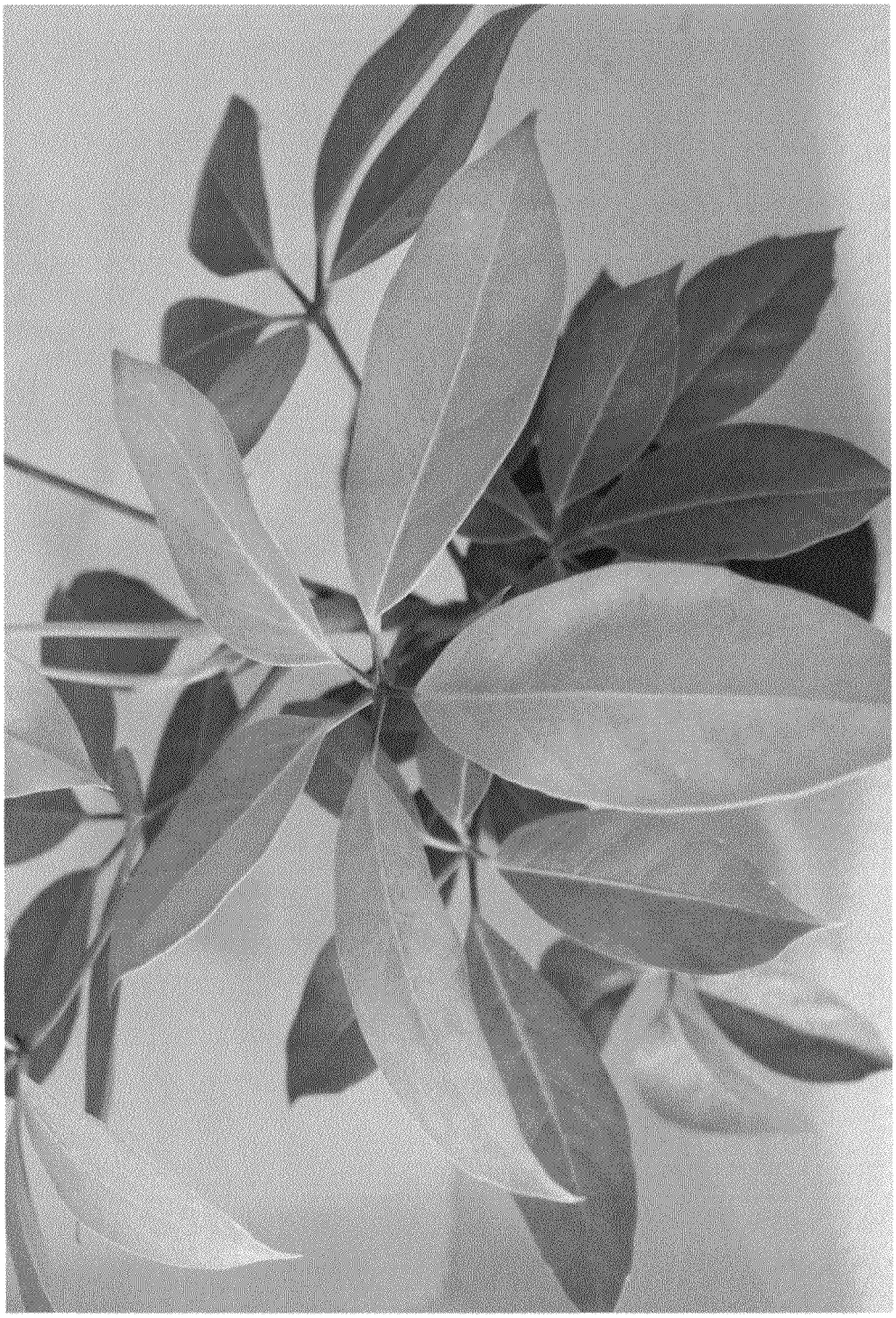

FIG. 3: Illustrates in full color a closer view of foliage of 'Amate Soleil'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'Amate Soleil' plants grown in a climate controlled greenhouse in Altha, Fla., USA. Temperatures ranged from 20° C. to 25° C. at night to 25° C. to 32° C. during the day. Light intensity was between 2500 and 3500 foot-candles. No artificial light, photoperiodic treatments were given to the plants. Measurements and numerical values represent averages of typical plant types.

Botanical classification: *Schefflera actinophylla* 'Amate Soleil'.

PROPAGATION

Time to initiate roots: 20 to 25 days at approximately 22° C.

Root description: Fleshy, thick, colored near RHS White 155A.

PLANT

Age of the plant described: Approximately 35 weeks.

Growth habit: Upright, somewhat outwardly spreading. Tender, tropical evergreen small tree or shrub.

Pot size of plant described: 6 inch.

Height: 36 cm.

Plant spread: 45 cm.

Growth rate: Moderate.

Branching characteristics: Plants described were not pinched, and have no lateral branches.

Length of stem: 21 cm.

Diameter of stem: 1.4 cm.

Characteristics of stem:

*Form.*—Squared.

*Color.*—Near RHS Yellow-Green N144D. Upper Stem lighter, near Yellow Green 145A.

*Texture.*—Glabrous. Oldest part of stem is rough with a somewhat woody texture. Irregular lenticels. Lenticels long and narrow, approximately 0.35 cm long and 0.1 cm wide. Lenticels colored near Yellow-Green 150D.

*Strength.*—Very strong.

Internode length: 1.8 cm to 3.0 cm.

FOLIAGE

Leaf:

*Arrangement.*—Spiral.

*Quantity.*—Approximately 15 palmately compound leaves, composed of 5 leaflets.

*Leaf size 6 inch pot.*—Compound Leaf: Leaflets arranged to form a nearly perfect circular shape. Average diameter: 25 cm.

*Leaflets.*—Average Length: 14 cm, including petiole. Average Width: 5 cm.

*Leaf size 8 inch pot.*—Compound Leaf: Leaflets arranged to form a nearly perfect circular shape. Average diameter: 38 cm.

*Leaflets.*—Average Length: 18 cm, including petiole. Average Width: 7 cm.

*Further leaflet description, 6 inch pots.*—Shape of blade: Elliptic. Apex: Acute to almost acuminate. Base: Attenuate. Margin: Entire. Texture of top surface: Glabrous. Texture of lower surface: Glabrous. Luster of top surface: Glossy to highly glossy. Luster of bottom surface: Matte. Aspect: Flat to very slightly undulating. Color: Young foliage upper side: Near RHS Yellow-Green N144B. Young foliage under side: Near RHS Yellow-Green N144A. Mature foliage upper side: Near RHS Yellow-Green 144A. Mature foliage under side: Near RHS Yellow-Green 144C. Venation: Type: Pinnate. Venation color upper side: Near RHS Yellow-Green N144B. Venation color under side: Near RHS Yellow-Green N144C. Petiole: Length: Average 12 cm. Diameter: 0.5 cm. Color: Near RHS Yellow-Green N144A, lightly flushed with Greyed-Red 181B. Texture: Glabrous. Leaflet Petiole: Length: 2.0 cm. Diameter: 0.3 cm. Color: Near RHS Yellow-Green N144B in the background, heavily flushed flushed with Greyed-Purple 186A. Texture: Glabrous.

FLOWER

Not observed to date.

OTHER CHARACTERISTICS

Disease/pest resistance: Neither resistance nor susceptibility to pathogens and pests common to *Schefflera* have been observed.

Temperature tolerance: The new variety tolerates temperatures between 0 to 40° C.

What is claimed is:

1. A new and distinct cultivar of *Schefflera* plant named 'Amate Soleil' as herein illustrated and described.

* * * * *